United States Patent
Hunter et al.

(10) Patent No.: US 6,716,442 B2
(45) Date of Patent: *Apr. 6, 2004

(54) PROCESS AND MEANS FOR THE ERADICATION OF FLEAS IN THE HABITATS OF SMALL MAMMALS

(75) Inventors: James S. Hunter, Athens, GA (US); Jean-Pierre Etchegaray, Toulouse (FR); Bruno Julia, Toulouse (FR); Philippe Jeannin, Tournefeuille (FR)

(73) Assignee: Merial, Lyons (FR)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/381,794

(22) PCT Filed: Mar. 25, 1998

(86) PCT No.: PCT/FR98/00601

§ 371 (c)(1), (2), (4) Date: Dec. 27, 1999

(87) PCT Pub. No.: WO98/42191

PCT Pub. Date: Oct. 1, 1998

(65) Prior Publication Data

US 2003/0007989 A1 Jan. 9, 2003

(30) Foreign Application Priority Data

Mar. 26, 1997 (FR) ............................................ 97 03709

(51) Int. Cl.$^7$ ................................................. A01N 25/02
(52) U.S. Cl. ....................... 424/405; 424/406; 424/407; 424/78.02; 514/407
(58) Field of Search .................. 514/341, 407, 514/460, 782; 424/405, 484, 485–502, 406, 78.02, 78.07

(56) References Cited

U.S. PATENT DOCUMENTS

| | | | | | |
|---|---|---|---|---|---|
| 5,567,429 A | * | 10/1996 | Senbo | ......................... | 424/405 |
| 5,712,295 A | * | 1/1998 | Mencke et al. | ............. | 514/338 |
| 5,939,441 A | * | 8/1999 | Stetter et al. | ................ | 514/341 |
| 6,096,329 A | * | 8/2000 | Jeannin | ....................... | 424/405 |

FOREIGN PATENT DOCUMENTS

| | | |
|---|---|---|
| DE | 44 43 888 | 6/1996 |
| DE | 195 19 007 | 11/1996 |
| EP | 0 214 477 | 3/1987 |
| EP | 0 255 803 | 2/1988 |
| EP | 0 295 117 | 12/1988 |
| EP | 0 516 590 | 12/1992 |
| EP | 0 682 869 | 11/1995 |
| FR | 2 713 889 | 6/1995 |
| WO | 96/16544 | 6/1996 |

OTHER PUBLICATIONS

Cooper et al. Use of Fipronil Vet. Record, Jul. 1996.*
Frontline Brochure '96.*
Abstract: Proc. Am. Assoc. Vet. Parasitol (1996), p. 52, "A Comparison of the Flea Control Efficacy of Frontline Spray Treatment . . . ", N.J. Meo, et al.

* cited by examiner

Primary Examiner—Neil S. Levy
(74) Attorney, Agent, or Firm—Frommer Lawrence & Haug, LLP; William S. Frommer; Thomas J. Kowalski

(57) ABSTRACT

Method for eradicating fleas in domestic or accommodation premises of a domestic or laboratory mammal is provided. The method involves topically applying, at least monthly, to the domestic or laboratory mammal, a parasitically effective amount of compound of Formula I.

11 Claims, No Drawings

PROCESS AND MEANS FOR THE ERADICATION OF FLEAS IN THE HABITATS OF SMALL MAMMALS

RELATED APPLICATIONS

This application was filed pursuant to 35 U.S.C. § 371 from international application PCT/FR98/00601, filed on Mar. 25, 1998, which, in turn, claims priority from French Application 97/03709, filed on Mar. 26, 1997.

The present invention relates to a procedure for the eradication of parasites, namely parasites of the order of Siphonaptera, especially fleas, such as, for example, *Ctenocephalides felis* and *canis*, but like-wise the other fleas of small mammals such as, for example, rabbits or laboratory animals.

The control of parasites of small domestic mammals, for example dogs and cats, and especially of fleas, is known to be extremely difficult.

Generally, it is attempted to control the animals themselves, either with the aid of flea collars containing various insecticides, or by topical application of preparations based on insecticides.

Nevertheless, the fleas always remain present in the environment of the animal, and especially in the premises of pets, such as domestic premises, kennels or catteries, as well as laboratories keeping animals.

The eradication of fleas in these premises with the aid of pesticides or agents for chemical treatment or the premises is a difficult operation and, except for permanently leaving the premises covered in an insecticidal substance, which can, in the long term, have an undoubted toxicity, reinfestation takes place rapidly.

Thus it only remains to regularly treat the animals with the aid of insecticides having a period of efficacy which is as great as possible, in order to reduce the periodicity and the cost of the treatments.

Thus the use has recently been proposed, for the treatment of fleas and of ticks in small animals, of topical preparations in the form of preparations for spraying or of concentrated preparations for point cutaneous application (spot on) whose active principle is formed by 1-[2,6-$Cl_2$-4-$CF_3$-phenyl]-3-CN-4-[SO—$CF_3$]-5-$NH_2$-pyrazole, whose non-proprietary name is fipronil.

In fact, the compounds belonging to the pyrazole, especially phenylpyrazole, families described in the Patents EP-A-295 217 and EP-A-352 944 have turned out to be extremely efficacious against fleas.

The period of anti-flea efficacy of fipronil, in the form of a concentrated solution for point application, called a spot on solution, can exceed 2 to 3 months in dogs and six weeks in cats.

In view of these performances, the users are naturally tempted to prolong the periods between two applications so as to benefit from this effect of long duration.

A possible explanation for the long duration of activity on the animal can be connected to the observation that fipronil dissolves in the sebum and the sweat glands to be released over a long time.

In a communication (Meo N.J. et al.; Proc. Am. Assoc. Vet. Parasitol (41 Meet., 52, 1996)), it was stated that there was a considerable increase in the percentage of non-reappearance of fleas in non-treated premises if the animals frequenting these premises (cats, dogs) received monthly administrations of sprays of the product Frontline® Spray containing fipronil.

The present invention proposes to simplify and to further improve this flea control.

A subject of the invention is thus a procedure for eradication of fleas in domestic or accommodation premises of mammals of small size, especially cats and dogs, characterized in that a concentrated topical preparation for point application, of the spot-on type in an efficaciously parasiticidal quantity of a compound of formula I or, optionally, of formula II is applied periodically to the animal or the animals of the premises considered, according to a monthly periodicity.

The formula I is the following formula:

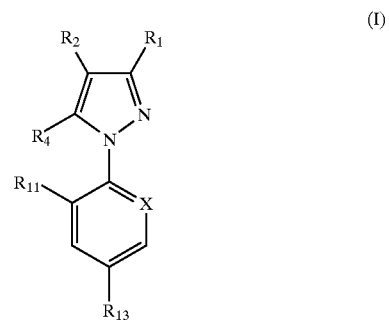

in which:

$R_1$ is CN or methyl or a halogen atom;

$R_2$ is $S(O)_n R_3$ or 4,5-dicyanoimidazol-2-yl or haloalkyl;

$R_3$ is alkyl or haloalkyl;

$R_4$ is a hydrogen or halogen atom; or an $NR_5 R_6$, $S(O)_m R_7$, C(O)—$R_7$, C(O)O—$R_7$, alkyl, haloalkyl or $OR_8$ radical or an —N=C($R_9$) ($R_{10}$) radical;

$R_5$ and $R_6$ independently are the hydrogen atom or an alkyl, haloalkyl, C(O)alkyl, alkoxycarbonyl or S(O)$_r$$CF_3$ radical; or $R_5$ and $R_6$ can together form a divalent alkylene radical which can be interrupted by one or two divalent heteroatoms, such as oxygen or sulphur;

$R_7$ is an alkyl or haloalkyl radical;

$R_8$ is an alkyl or haloalkyl radical or a hydrogen atom;

$R_9$ is an alkyl radical or a hydrogen atom;

$R_{10}$ is a phenyl or heteroalkyl group which is optionally substituted by one or more halogen atoms or groups such as OH, —O-alkyl, —S-alkyl, cyano or alkyl;

$R_{11}$ and $R_{12}$ are, independently of one another, a hydrogen or halogen atom, or optionally CN or $NO_2$;

$R_{13}$ is a halogen atom or a haloalkyl, haloalkoxy, S(O)$_q$$CF_3$ or $SF_5$ group;

m, n, q and r are, independently of one another, an integer equal to 0, 1 or 2;

X is a trivalent nitrogen atom or a C—$R_{12}$ radical, the three other valencies of the carbon atom being part of the aromatic ring;

with the reservation that when $R_1$ is methyl, $R_3$ is haloalkyl, $R_4$ is $NH_2$, $R_{11}$ is Cl, $R_{13}$ is $CF_3$ and X is N; or when $R_2$ is 4,8-dicyanoimidazol-2-yl, $R_4$ is Cl, $R_{11}$ is Cl, $R_{13}$ is $CF_3$ and X is =C—Cl.

The formula II is the following formula:

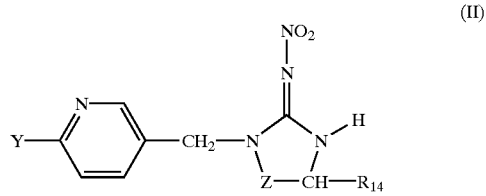

where Y is hydrogen or halogen
$R_{14}$ is hydrogen or methyl
and Z is —$(CH_2)_n$— with n=1 or 2.
Preferably, in the formula (I),
$R_1$ is CN or methyl;
$R_2$ is $S(O)_nR_3$;
$R_3$ is haloalkyl or ethyl
$R_4$ is a hydrogen or halogen atom; or an $NR_5R_6$, $S(O)_mR_7$, $C(O)R_7$, alkyl, haloalkyl or $OR_8$ radical or an —N=C($R_9$) ($R_{10}$) radical;
$R_5$ and $R_6$ independently are the hydrogen atom or an alkyl, haloalkyl, C(O)alkyl, $S(O)_rCF_3$ radical; or $R_5$ and $R_6$ can together form a divalent alkylene radical which can be interrupted by one or two divalent heteroatoms, such as oxygen or sulphur;
$R_{11}$ and $R_{12}$ are, independently of one another, a hydrogen or halogen atom;
with the reservation that when $R_1$ is methyl, $R_3$ is haloalkyl, $R_1$ is $NH_2$, $R_{11}$ is Cl, $R_{13}$ is $CF_3$ and X is N.

Compounds of formula (I) which will be considered are very particularly those in which $R_1$ is CN. Compounds will also be considered in which $R_{13}$ is haloalkyl, preferably $CF_3$, or $R_2$ is $S(O)_nR_3$ with $R_3$ being haloalkyl or X=C—$R_{12}$, $R_{12}$ being a halogen atom. It is also preferred that $R_{11}$ is a halogen atom.

A preferred class of compounds of formula (I) is formed by the compounds where $R_1$ is CN, $R_3$ is haloalkyl, $R_4$ is $NH_2$, $R_{11}$ and $R_{12}$ are independently of one another a halogen atom, and/or $R_{13}$ is haloalkyl.

The alkyl radicals of the definition of the compounds of formulae (I) generally comprise from 1 to 6 carbon atoms. The ring formed by the divalent alkylene radical representing $R_5$ and $R_6$ as well as the nitrogen atom to which $R_5$ and $R_6$ are attached is generally a ring with 5, 6 or 7 members.

A compound of formula (I) which is very particularly preferred in the invention is
1-[2,6-$Cl_2$-4-$CF_3$-phenyl]-3-CN-4-[SO—$CF_3$]-5-$NH_2$-pyrazole, called fipronil below.

Among numerous other advantageous compounds, it is possible to mention 1-[2,6-$Cl_2$-4-$CF_3$-phenyl]-3-CN-4-[SO—$C_2H_5$]-5-$NH_2$-pyrazole.

The compounds of formula (I) can be prepared according to one or other of the processes described in the Patent Applications WO-A-87/3781, 93/6089, 94/21606 or European EP-A-0 295 117, or any other procedure dependent on the competence of the specialist in chemical synthesis. For the chemical preparation of the products of the invention, the person skilled in the art is considered as having at his disposition, among other things, all the contents of "Chemical Abstracts" and documents which are cited there.

Preferably, in the compound of formula (II) Y=Cl, $R_{14}$=H and n=1, that is to say
1-[(6-chloro-3-pyridinyl)methyl]-4,5-dihydro-N-nitro-1H-imidazol-2-amine or imidaclopride.

The compounds of the formula (II) can be prepared by the corresponding procedures described, for example, in EP-A-0 192 060.

Monthly periodicity is ideally understood as meaning one treatment every month but it is understood that the invention can be practised at a higher rate, for example twice weekly or every three weeks, or optionally, but in a non-preferred fashion, a slightly lower rate, for example every five weeks.

The preferred periodicity is the monthly periodicity, a higher rate resulting in a needless consumption. In addition, the monthly rate has the advantage of allowing the user to memorize and to plan the applications.

When the premises contain several animals, it is preferable, and more simple, to treat all the animals at the same time.

The efficaciously parasiticidal quantity, in the sense of the invention, is the quantity used to eradicate fleas on the animal itself and may thus correspond to doses already recommended for the topical treatment of the animal for the formulations already used commercially. Such a dose must be able to protect the animal itself for a period of at least one month.

The dose of active compound is, preferably, between 0.3 and 60 mg, and preferably between 5 and 15 mg per kilo of body weight per treated animal.

The treatment according to the invention can be carried out continuously, optionally taking account of the infestation seasons where infestation is seasonal. Such a continuous treatment is preferred for the premises where numerous animal entries occur, for example farms, kennels, catteries or veterinary clinics.

In a particularly preferred manner, concentrated preparations for point application of "spot on" type, formulae for which the preparation volume applied to the animal is of the order of 0.3 to 1 ml, preferably 0.5 ml for cats, and of the order of 0.3 to 3 ml for dogs, as a function of the weight of the animal will be preferred.

This preparation can contain, apart from the active principle itself, a crystallization inhibitor, an organic solvent and an organic cosolvent.

Preferably, the active compound, especially the compound of formula I, can be present in the formulation at the rate of a concentration of 1 to 20% and preferably of 5 to 15% (percentage in weight by volume).

The object of the procedure according to the invention can be non-therapeutic, involving on the one hand cleaning the hair and the skin of the animals by eliminating the parasites present and by avoiding their waste and excrement so that the animal has a coat which is pleasant to the eye and to the touch, likewise consisting of suppressing the appearance and the development of fleas in the premises inhabited by the animal.

The object can also be therapeutic when it consists in treating a parasitosis having pathogenic consequences.

The concentrated compositions for point application can advantageously comprise:
  a) the compound of formula I
  b) a crystallization inhibitor, especially present at a rate of 1 to 20% (W/V), preferably of 5 to 15%, this inhibitor responding to the test according to which:
    0.3 ml of a solution comprising 10% (W/V) of the compound of formula (I) in the solvent defined under c) below, as well as 10% of this inhibitor, are placed on a glass slide at 20° C. for 24 hours, following which few or no crystals, especially less than 10 crystals, preferably 0 crystals, are observed with the naked eye on the glass slide,
  c) an organic solvent having a dielectric constant of between 10 and 35, preferably between 20 and 30, the content of this solvent c) in the total composition preferably representing the remainder to 100% of the composition, d) an organic cosolvent having a boiling point lower than 100° C., preferably lower than 80° C., and having a dielectric constant of between 10 and 40, preferably between 20 and 30; this cosolvent can advantageously be present in the composition according to a weight/weight (W/W) ratio of d)/c) of between $1/15$ and $1/2$. The solvent is volatile in order to serve especially to promote drying and is miscible with water and/or with the solvent c).

Although this is not preferred, the composition for point application can optionally comprise water, especially at a rate of 0 to 30% (volume per volume V/V), in particular of 0 to 5%.

The composition for point application can also comprise an antioxidant agent intended to inhibit oxidation in the air, this agent especially being present at a rate of 0.005 to 1% (W/V), preferably of 0.01 to 0.05%.

The compositions according to the invention intended for pets, especially dogs and cats, are applied by spotting on; this generally consists of a localized application on a surface zone of less than 10 cm$^2$, especially of between 5 and 10 cm$^2$, in particular at two points and preferably localized between the shoulders of the animal. After deposition, the composition diffuses, especially over all the body of the animal, then dries without crystallizing, nor modifying the appearance especially absence of any whitish deposit or dusty appearance) nor affecting the coat.

The compositions for point application according to the invention are particularly advantageous by virtue of their efficacy, their rapidity of action, as well as by virtue of the pleasant appearance of the hair of the animals after application and drying.

As organic solvent c) which can be used in the invention, it is possible to mention in particular: acetone, acetonitrile, benzyl alcohol, butyl diglycol, dimethylacetamide, dimethylformamide, dipropylene glycol n-butyl ether, ethanol, isopropanol, methanol, ethylene glycol monoethyl ether, ethylene glycol monomethyl ether, monomethylacetamide, dipropylene glycol monomethyl ether, liquid polyoxyethylene glycols, propylene glycol, 2-pyrrolidone, especially N-methyl-pyrrolidone, diethylene glycol monoethyl ether, ethylene glycol, diethyl phthalate, or a mixture of at least two of these.

As crystallization inhibitor b) which can be used in the invention, it is possible to mention in particular:

polyvinylpyrrolidone, polyvinyl alcohols, copolymers of vinyl acetate and vinylpyrrolidone, polyethylene glycols, benzyl alcohol, mannitol, glycerol, sorbitol, polyethoxylated sorbitan esters; lecithin, carboxymethylcellulose sodium, acrylic derivatives such as methacrylates and others, anionic surfactants such as alkali metal stearates, especially of sodium, of potassium or of ammonium; calcium stearate; triethanolamine stearate; sodium abietate; alkylsulphates, especially sodium laurylsulphate and sodium cetylsulphate; sodium dodecylbenzenesulphonate, sodium dioctylsulphosuccinate; fatty acids, especially those derived from copra oil, cationic surfactants such as water-soluble quaternary ammonium salts of formula $N^+R'R''R'''R''''$, $Y^-$ in which the R radicals are optionally hydroxylated hydrocarbon radicals, and $Y^-$ is an anion of a strong acid, such as halide, sulphate and sulphonate anions; cetyltrimethylammonium bromide is among the cationic surfactants utilizable, the amine salts of formula $N^+R'R''R'''$ in which the R radicals are optionally hydroxylated hydrocarbon radicals; octadecylamine hydrochloride is among the cationic surfactants utilizable, the non-ionic surfactants such as optionally polyethoxylated sorbitan esters, in particular Polysorbate 80, polyethoxylated alkyl ethers; polyethylene glycol stearate, polyethoxylated castor oil derivatives, polyglycerol esters, polyethoxylated fatty alcohols, polyethoxylated fatty acids, copolymers of ethylene oxide and propylene oxide, amphoteric surfactants such as substituted lauryl betaine compounds, or preferably a mixture of at least two of these.

Particularly preferably, a crystallization inhibitor pair will be used, namely the combination of a surface-active agent. These agents will especially be chosen from the compounds mentioned as crystallization inhibitor b).

Among the filmogenic agents of particularly interesting polymeric type, it is possible to mention:

different grades of polyvinylpyrrolidone, polyvinyl alcohols, and copolymers of vinyl acetate and vinylpyrrolidone.

As far as surface-active agents are concerned, very particular mention will be made of non-ionic surfactants, preferably polyethoxylated esters of sorbitan and especially the different grades of Polysorbates, for example Polysorbate 80.

The filmogenic agent and surface-active agent will especially be able to be incorporated in close or identical quantities in the limit of total quantities of crystallization inhibitor otherwise mentioned.

The pair thus formed remarkably ensures the objectives of absence of crystallization on the hair and of maintenance of the cosmetic appearance of the coat, that is to say without tendency to sticking or to sticky appearance, despite the high concentration of active material.

As cosolvent d), it is possible to mention in particular: absolute ethanol, isopropanol, methanol.

As antioxidant agent, conventional agents are especially used, such as: butylhydroxyanisole, butylhydroxytoluene, ascorbic acid, sodium metabisulphite, propyl gallate, sodium thiosulphate, or a mixture of at least two of these.

The compositions for point application according to the invention are usually prepared by simple mixing of the constituents as defined above; advantageously, a start is made by mixing the active material in the principal solvent, and the other ingredients or adjuvants are then added.

In an advantageous manner, it is possible to provide for ready-for-use compositions, prepared for animals of 1–10, 10–20, 20–40 kg respectively.

In a particularly preferred manner, the composition according to the invention can be present in the form of a concentrated emulsion or solution suspension for point application on a small cutaneous zone of the animal, generally between the two shoulders (spot-on type solution).

The procedure according to the invention can likewise comprise, in addition, the administration of another parasiticide, preferably at the same rate, and preferably administered concomitantly, and preferentially with the aid of a single composition comprising a mixture or a combination of this parasiticide and of an insecticide of formula I or II. These combined parasiticides are not known in themselves to have an activity allowing them to act directly on the insects in the stage thereof removed from the animal, but they can be useful for further increasing the efficacy against fleas resident on the animal and likewise for reducing the possible risks of insecticide resistance occurring.

Among these combined parasiticides it is possible especially to mention the compounds mimicking juvenile hormones, especially:

azadirachtin—Agridyne
diofenolan (Ciba Geigy)
fenoxycarb (Ciba Geigy)
hydroprene (Sandoz)
kinoprene (Sandoz)
methoprene (Sandoz)
pyriproxyfene (Sumitomo/Mgk)
tetrahydroazadirachtin (Agridyne)
and 4-chloro-2-(2-chloro-2-methylpropyl)-5-(6-iodo-3-pyridylmethoxy)pyridazine-3(2H)-one and chitin synthesis inhibitors, especially:
chlorfluazuron (Ishihara Sangyo)
cyromazine (Ciba Geigy)
diflubenzuron (Solvay Duphar)
fluazuron (Ciba Geigy)
flucycloxuron (Solvay Duphar)
flufenoxuron (Cyanamid)
hexaflumuron (Dow Elanco)
lufenuron (Ciba Geigy)
novaluron (Isagro, Italy)
tebufenozide (Rohm & Haas)
teflubenzuron (Cyanamid)
triflumuron (Bayer)

these compounds being defined by their international non-proprietary name (The Pesticide Manual, 10th edition, 1994, Ed. Clive Tomlin, Great Britain).

It is possible to mention, likewise as chitin synthesis inhibitors, compounds such as 1-(2,6-difluorobenzoyl)-3-(2-fluoro-4-(trifluoromethyl)phenylurea, 1-(2,6-difluorobenzoyl)-3-(2-fluoro-4-(1,1,2,2-tetrafluoroethoxy)phenylurea, 1-(2,6-difluorobenzoyl)-3-(2-fluoro-4-(trifluoromethyl)phenylurea.

The preferred combined compounds are methoprenes, pyriproxyphenes, hydroprene, cyromazine, lufenuron, novaluron and 1-(2,6-difluorobenzoyl)-3-(2-fluoro-4-(trifluoromethyl)phenylurea.

It is preferred that the administration of the two types of compounds is concomitant and preferably simultaneous.

Preferably, the treatment is conducted so as to administer to the animal a dose of 0.1 to 40, and especially of 1 to 20, mg/kg for the derivative of formula I or II and a dose of 0.1 to 40, especially 1 to 30, mg/kg for the combined compound.

The preferred doses are from 5 to 15 mg/kg for the compound of formula I and from 0.5 to 15 mg/kg for the combined compounds.

The proportions by weight of the compound of formula I or II and of the combined compound are, preferably, between 80/20 and 20/80.

In another form of preparation, the combined parasiticide can be an endectocidal parasiticide of macrocyclic lactone type.

Preferably, this parasiticide is chosen from the group formed by the avermectins, ivermectin, abamectin, doramectin, moxydectin, the milbemycins and the derivatives of these compounds.

The structure, the characteristics and the processes of production of these compounds are well known to the person skilled in the art and it will be possible to refer to the widely available technical and commercial literature. For the avermectins, ivermectin and abamectin, it is possible to refer, for example, to the work "Ivermectin and Abamectin", 1989 by M. H. FISCHER and H. MROZIK, William C. CAMPBELL, ed. Springer Verlag or ALBERT-SCHÖNBERG et al. (1981) "Avermectin Structure Determination". J. Am. Chem. Soc. 103: 4216–4221. For doramectin, it will be possible to consult, especially, "Veterinary Parasitology" vol. 49 No. 1, July 1993: 5–15. For the milbemycins it will be possible to refer, inter alia, to DAVIES H. G. et al., 1986, "Avermectins and Milbemycins". Nat. Prod. Rep. 3: 87–121, Mrozik H. et al., 1983, Synthesis of milbemycins from avermectins, Tetrahedron lett. 24: 5333–5336 as well as U.S. Pat. No. 4,134,973.

The administration of the two types of compounds can be concomitant and preferably simultaneous in the form of a single composition.

The efficacious quantity of endectocidal compound is preferably from between 0.1 µg, preferentially 1 µg, and 1 mg, and in a particularly preferred manner 5 to 200 µg/kg of animal weight. The proportions by weight between the compound of formula (I) or (II) and the endectocidal compound are preferably between 5/1 and 10,000/1.

The mechanisms by which the fleas disappear from the premises themselves are not well known and the efficacy of the invention is particularly surprising.

An object of the present invention is likewise packed outfits or kits comprising one or more units of compositions which can be used in the invention representing a plurality of monthly doses intended to be successively administered to an animal for carrying out the procedure for a long period, for example, according to the country, for a period of one year or for a period of one season of flea infestation.

Preferably, this kit contains a plurality of different monthly unit doses, for example 3 or 6 (for one season) or 12 (for one year) different doses contained in as many containers of spot on or pour on type. In this form of implementation, several kit versions are provided as a function of the weight of the animals.

The kit likewise comprises means of explanation such as a note for ensuring the periodicity of the use of the doses.

In another form of implementation, the different doses can be contained in a single container equipped with means for ensuring the application of a dose corresponding to the quantity intended to be administered monthly. This means can be, for example, a metering pump or valve ensuring the delivery of a precise dose. It can also, more simply, be formed of a graduation with regard to a transparent container surface, allowing the liquid volume of composition which remains in the container to be known.

An object of the invention is likewise the use of a compound of formula I or of formula II for the preparation of a composition for the eradication of fleas in domestic or accommodation premises of mammals of small size, especially cats and dogs, by periodic application to the animal or the animals of the premises considered of a topical preparation as defined hereinabove in an efficaciously parasiticidal quantity of a compound of formula I, or optionally of formula II, according to a monthly periodicity.

Other advantages and characteristics of the invention will become apparent from reading the following description, by way of non-limiting example.

EXAMPLE 1

The test used dogs in good health.

The dogs were divided by groups of three dogs into enclosures of area approximately 4.80 m long (16 feet) and 1.5 m wide (5 feet) each containing a shelter and soil especially favourable to the development of the immature stages of the fleas (*Ctenocephalides felis*). All the dogs were voluntarily and identically preinfested and then regularly infested by fleas at a rate such that the total number of fleas carried by each animal of the control group A did not fall significantly below 20.

A total of 18 dogs, that is to say six enclosures, was allocated to the control group A.

A group C of six dogs (2 enclosures) preinfested in this way received the treatment according to the invention by application of a cutaneous point solution having a concentration of 10% of fipronil.

The doses of concentrated composition for local cutaneous application of fipronil were as follows:

| Weight of the animal | Doses |
|---|---|
| 5–10 kg | 0.67 ml |
| 10–20 kg | 1.34 ml |
| 20–40 kg | 2.68 ml |

The animals of group C were treated on day 0 and then every 28 days, that is to say the days 28, 56 and 84.

The checks (weekly counting of the eggs, counting on the body in weeks 1, 3, 5, 7, 9 and counting on the comb in weeks 2, 4, 6, 8, 10, 11, 12) showed a rate of control of the infestation equal to 100%.

A similar test on cats gave the same results, that is to say a total absence of reinfestation.

What is claimed is:

1. A method for the eradication of fleas in domestic or accommodation premises of a domestic or laboratory mammal, comprising topically applying, at least monthly, to a localized region having a surface area of 10 cm² or less on the domestic or laboratory mammal, a parasitically effective amount of a spot-on topical preparation comprising a veterinarily acceptable vehicle and a compound of Formula I:

Formula I:

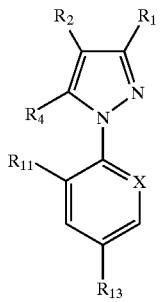

in which:

$R_1$ is CN;
$R_2$ is $S(O)_n R_3$;
$R_3$ is haloalkyl;
$R_4$ is $NH_2$;
$R_{11}$ and $R_{12}$ are, independently of one another a halogen atom;
$R_{13}$ is a haloalkyl;
n is an integer equal to 0, 1 or 2;
X is a C—$R_{12}$ radical;
wherein, when the preparation is so applied to the mammal, through the action of the compound and the vehicle, the compound diffuses over the mammal's body, and then dries without crystallization and without modifying the mammal's appearance and coat, and wherein said mammal is selected from the group consisting of canine and feline.

2. The method according to claim 1, wherein $R_{13}$ is $CF_3$.

3. The method according to claim 1, wherein the compound of Formula (I) is 1-[2,6-$Cl_2$-4-$CF_3$-phenyl]-3-CN-4-[SO—$CF_3$]-5-$NH_2$-pyrazole.

4. The method according to claim 1, wherein the dose of the compound is between 0.3 and 60 mg/kg of treated mammal 5. The method according to claim 1, wherein the dose of the compound is between 5 and 15 mg/kg of treated animal.

6. The method according to claim 1, wherein the amount of the topical preparation applied to felines is about 0.3 to 1 ml/kg.

7. The method according to claim 6, wherein the amount of the topical preparation applied to felines is about 0.3 to 0.5 ml/kg.

8. The method according to claim 1, wherein the amount of the topical preparation applied to canines is about 0.3 to 3 ml/kg.

9. The method according to claim 1, wherein the topical preparation further comprises a crystallization inhibitor, an organic solvent and an organic co-solvent.

10. The method according to claim 1, wherein when the premises contain several mammals, all the mammals are treated at the same time.

11. The method according to claim 1, wherein the treatment is carried out continuously, optionally taking account of the infestation seasons where infestation is seasonal.

* * * * *